US012181386B2

(12) United States Patent
Jenkins et al.

(10) Patent No.: US 12,181,386 B2
(45) Date of Patent: Dec. 31, 2024

(54) LIPID-PRESERVING REFRACTIVE INDEX MATCHING FOR PROLONGED IMAGING DEPTH FOR TRANSPARENT TISSUE SAMPLE AND COMPOSITION (71) Applicants: Case Western Reserve University, Cleveland, OH (US); University Hospitals Cleveland Medical Center, Cleveland, OH (US)

(72) Inventors: Michael W. Jenkins, Cleveland, OH (US); Yehe Liu, Cleveland, OH (US)

(73) Assignees: CASE WESTERN RESERVE UNIVERSITY, Cleveland, OH (US); UNIVERSITY HOSPITALS CLEVELAND MEDICAL CENTER, Cleveland, OH (US); VANDERBILT UNIVERSITY, Nashville, TN (US)

( * ) Notice: Subject to any disclaimer, the term of this patent is extended or adjusted under 35 U.S.C. 154(b) by 1207 days.

(21) Appl. No.: 16/760,652

(22) PCT Filed: Nov. 9, 2018

(86) PCT No.: PCT/US2018/060078
§ 371 (c)(1),
(2) Date: Apr. 30, 2020

(87) PCT Pub. No.: WO2019/094753
PCT Pub. Date: May 16, 2019

(65) Prior Publication Data
US 2021/0372890 A1 Dec. 2, 2021

Related U.S. Application Data (60) Provisional application No. 62/583,649, filed on Nov. 9, 2017.

(51) Int. Cl.
G01N 1/30 (2006.01)
G01N 33/50 (2006.01)

(52) U.S. Cl.
CPC ........... *G01N 1/30* (2013.01); *G01N 33/5082* (2013.01)

(58) Field of Classification Search
CPC ............................. G01N 1/30; G01N 33/5082
See application file for complete search history.

(56) References Cited

U.S. PATENT DOCUMENTS

| 6,472,216 | B1 | 10/2002 | Chiang |
| 11,130,931 | B2 * | 9/2021 | Lai ......................... C11D 7/263 |
| 2013/0045503 | A1 | 2/2013 | Miyawaki et al. |
| 2014/0087419 | A1 | 3/2014 | Miyawaki et al. |
| 2014/0178927 | A1 | 6/2014 | Miyawaki et al. |
| 2017/0199104 | A1 | 7/2017 | Gradinaru et al. |

FOREIGN PATENT DOCUMENTS

| WO | 2014/115206 A1 | 7/2014 |
| WO | 2015/041755 A1 | 3/2015 |
| WO | 2016/147812 A1 | 9/2016 |

OTHER PUBLICATIONS

Boothe et al. A tunable refractive index matching medium for live imaging cells, tissues and model organisms. eLife Jul. 14, 2017;6: e27240. doi: 10.7554/eLife.27240, pp. 1-15. (Year: 2017).*
PCT International Search Report and Written Opinion for corresponding International Application Serial No. PCT/US2018/060078, mailed Mar. 11, 2019, pp. 1-70.

* cited by examiner

*Primary Examiner* — Shafiqul Haq
(74) *Attorney, Agent, or Firm* — Tarolli, Sundheim, Covell & Tummino LLP (57) ABSTRACT The present disclosure relates to an optical clearing method called lipid-preserving index matching for prolonged imaging depth (LIMPID). The optical clearing method can include simply immersing a sample in an optical clearing solution before imaging (e.g., with microscopy or optical coherence tomography). The optical clearing solution can include water; an iodine-containing non-ionic radiocontrast agent; and urea.

13 Claims, 7 Drawing Sheets

LIPID-PRESERVING REFRACTIVE INDEX MATCHING FOR PROLONGED IMAGING DEPTH FOR TRANSPARENT TISSUE SAMPLE AND COMPOSITION

RELATED APPLICATION

This application claims priority to U.S. Provisional Application Ser. No. 62/583,649, filed Nov. 9, 2017, entitled "WATER SOLUBLE LIPID-PRESERVING OPTICAL CLEARING AGENT FOR IMPROVING TRANSPARENCY OF BIOLOGICAL SAMPLES", the entirety of which is hereby incorporated by reference for all purposes.

GOVERNMENT FUNDING

This invention was made with government support under HL126747 awarded by the National Institutes of Health. The government has certain rights in the invention.

TECHNICAL FIELD

The present disclosure relates generally to optical clearing and, more specifically, to an optical clearing method called lipid-preserving index matching for prolonged imaging depth (LIMPID).

BACKGROUND

Imaging techniques like three-dimensional (3-D) microscopy and optical coherence tomography often suffer from restricted imaging depth in biological tissue, which appears opaque. The opacity of the biological tissue is due to light scattering on interfaces between lipids and other tissue compounds with different refractive indices. Optical clearing is a process that makes biological tissues more optically transparent, while keeping internal structure intact. Several optical clearing techniques have been developed to reduce such scattering and, thereby, increase imaging depth, enabling imaging of large regions of interest. These optical clearing techniques include organic solvent-based clearing techniques, lipid extraction after hydrogel embedding techniques, and aqueous solution based techniques. These optical clearing techniques suffer from one or more limitations, including requiring a long time, requiring fancy instruments, suffering from limited dye compatibility, and requiring extra work.

SUMMARY

In an aspect, the present disclosure can include an optical clearing method called lipid-preserving index matching for prolonged imaging depth (LIMPID). The method can include immersing a sample in an optical clearing solution before imaging. The sample can be previously labeled for the imaging. The optical clearing solution includes water, an iodine-containing non-ionic radiocontrast agent; and urea. The iodine-containing non-ionic radiocontrast agent and urea work together in a synergistic manner to strengthen the clearing capability of the optical clearing solution. The optical clearing solution has an adjustable refractive index and osmolality, which improves the image quality by matching the refractive index to optical hardware and eliminating tissue distortions.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

I. Definitions

Unless otherwise defined, all technical terms used herein have the same meaning as commonly understood by one of ordinary skill in the art to which the present disclosure pertains.

As used herein, the singular forms "a," "an" and "the" can also include the plural forms, unless the context clearly indicates otherwise.

As used herein, the terms "comprises" and/or "comprising," can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

As used herein, the terms "first," "second," etc. should not limit the elements being described by these terms. These terms are only used to distinguish one element from another. Thus, a "first" element discussed below could also be termed a "second" element without departing from the teachings of the present disclosure. The sequence of operations (or acts/steps) is not limited to the order presented in the claims or figures unless specifically indicated otherwise.

As used herein, the term "imaging" can refer to the act of creating a visual representation of an interior of at least a portion of a sample for analysis. When the imaging is referred to as being "three-dimensional (3D)", a volumetric visual representation of the interior of at least the portion of the sample is created. Example imaging modalities can include, but are not limited to, confocal microscopy, light-sheet microscopy, two-photon microscopy, optical coherence tomography, and the like.

As used herein, the term "lipid-preserving index matching for prolonged imaging depth (LIMPID)" can refer to an optical clearing method employing a clearing agent that includes at least water; an iodine-containing, non-ionic radiocontrast agent; and urea at varying concentrations. The clearing agent can further include a refractive index adjustment agent, an osmotic pressure adjustment agent, and/or a detergent.

As used herein, the terms "optical clearing" and "clearing" can refer to the act of minimizing light scatter from a sample by exposing the sample to a clearing agent.

As used herein, the term "sample" can refer to a biological specimen taken from a subject. For example, the sample can be a tissue sample excised from a subject.

As used herein, the term "weight percent" refers to a number of grams of solute in 100 mL of solution.

As used herein, the term "subject" can refer to any warm-blooded organism including, but not limited to, a human being, a pig, a rat, a mouse, a bird, a dog, a cat, a goat, a sheep, a horse, a monkey, an ape, a rabbit, a cow, etc.

II. Overview

The present disclosure includes an optical clearing method called lipid-preserving index matching for prolonged imaging depth (LIMPID—a synonym for clear). Clearing a tissue sample with LIMPID can increase imaging depth when imaging with confocal microscopy, light-sheet microscopy, two-photon microscopy, optical coherence tomography, or the like, allowing investigation of the three-dimensional (3-D) organization of many complex structures. A significant benefit of LIMPID over other clearing methods is it simplicity: the clearing solution is easy to make and the clearing process only requires a single step (immersion of the sample, which can be labeled or preprocessed, in the clearing agent before imaging). LIMPID allows for speedy clearing that is compatible with many different instruments and sample preparation techniques, and increases both the imaging depth and the signal to noise ratio (SNR).

The LIMPID clearing agent includes water, an iodine-containing, non-ionic radiocontrast agent, and urea. Water is the solvent for the other ingredients. However, the LIMPID clearing agent has a higher clearing capability than most existing water-soluble optical clearing agents. The iodine-containing, non-ionic radiocontrast agent (e.g., iodixanol, which can be in solution with a polyhydric alcohol) can be used for index matching and reducing scattering from lipids within the sample. Urea is a protein denaturation and super-hydration agent that reduces scattering from proteins and aids in antigen retrieval. Use of the iodine-containing, non-ionic radiocontrast agent together with the urea does not damage lipid content or reduce the speed of diffusion, but instead produces a synergistic effect on speed and clearing capability. The LIMPID clearing agent can also include a refractive index adjustment agent and/or an osmotic pressure adjustment agent, which can help to improve image quality. In some instances, the LIMPID clearing agent can also include a detergent to help permeabilization of cells within the sample.

III. Systems

One aspect of the present disclosure can include a system 10 (FIG. 1) that can be used to perform an optical clearing method called lipid-preserving index matching for prolonged imaging depth (LIMPID). A significant benefit of LIMPID over other clearing methods is its simplicity. The clearing solution is easy to make and the clearing process only requires one step (immersion of the labeled sample in the clearing agent before imaging).

Figure 1:
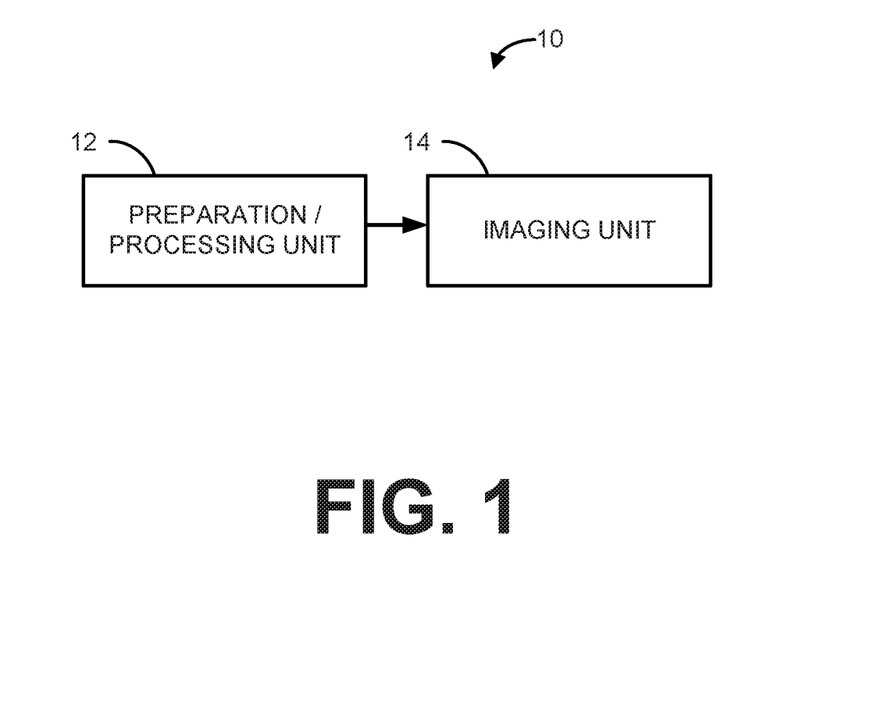
FIG. 1 is a diagram showing a system that can be used to perform an optical clearing method called lipid-preserving index matching for prolonged imaging depth (LIMPID) in accordance with an aspect of the present disclosure.

The system 10 includes a preparation/processing unit 12 and an imaging unit 14. One or more of the preparation/processing unit 12 and the imaging unit 14 can perform computer-aided actions, which are stored in one or more non-transitory memory units and executed by one or more processors. In some instances, the preparation/processing unit 12 and the imaging unit 14 unique entitles (e.g., located at different places). However, in other instances, functionalities of one or more of the preparation/processing unit 12 and the imaging unit 14 can be combined.

The preparation/processing unit 12 can perform optical clearing on a prepared sample using LIMPID. LIMPID provides a simple and cost effective way to evaluate properties (e.g., morphology, 3D organization, etc.) of a sample. The imaging unit 14 can record images of the optically cleared prepared sample that can be used in the evaluation of the sample. The imaging unit 14 can include hardware for an imaging modality, like microscopy (e.g., confocal microscopy, light-sheet microscopy, two-photon microscopy, etc.), optical coherence tomography (OCT), or any other imaging modality that would benefit from the increased image depth achieved through optical clearing.

Figure 2:
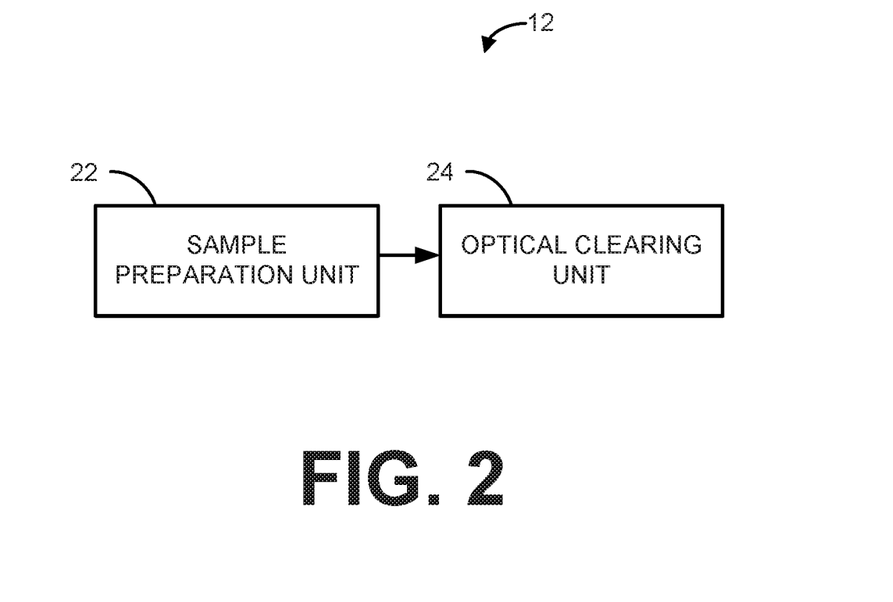
FIG. 2 is a diagram showing an example configuration of the preparation/processing unit in FIG. 1.

As shown in FIG. 2, the preparation/processing unit 12 can include an optical clearing unit 24 that can apply the LIMPID clearing agent to the sample. As an example, the sample can be immersed in a solution of the LIMPID clearing agent. The sample can be immersed for a time sufficient for the clearing to occur in the sample (the time is variable based on the size and depth of the sample) before the sample is imaged. In some instances, the preparation/processing unit 12 can include a sample preparation unit 22 that can prepare the sample for clearing and/or imaging. For example, the sample preparation unit 22 can facilitate the performance of labeling, staining, adding contrast agent, or any other pre-imaging task necessary for clearing and/or imaging.

The clearing agent solution includes at least water, an iodine-containing, non-ionic radiocontrast agent, and urea. The water is a solvent for all other ingredients. The iodine-containing, non-ionic radiocontrast agent and the urea, when used together, can provide a synergistic effect of decreasing the speed required to clear the sample and increasing the clearing capability (e.g., increasing the depth of the sample that is cleared in the time).

The iodine-containing, non-ionic radiocontrast agent is added to the water to reduce scattering from lipids, as well as provides index matching. For example, the iodine-containing, non-ionic radiocontrast agent can include 40 to 80 weight percent iodixanol in solution with 0 to 20 weight percent polyhydric alcohol (such as glycerol, poly(ethelyne glycol), triethanolamine, and quadrol (N,N,N',N-Trtrakis(2-Hydroxypropyl)ethylenediamine) In some instances, the iodine-containing, non-ionic radiocontrast agent can include 50 to 70 weight percent iodixanol. In other instances, the iodine-containing, non-ionic radiocontrast agent can include 57 to 64 weight percent iodixanol. In further instances, the iodine-containing, non-ionic radiocontrast agent can include about 60 weight percent iodixanol.

The urea is added to the water as a protein denaturation and super-hydration agent that reduces scattering from proteins. The urea can be added to the water at a concentration of 10 to 50 weight percent. In some instances, the urea can be added to the water at a concentration of 25 to 45 weight percent. In other instances, the urea can be added to the water at a concentration of 30 to 50 weight percent. In still other instances, the urea can be added to the water at a concentration of 35 to 45 weight percent.

In some instances, the clearing agent solution can have an adjustable refractive index and/or an adjustable osmolality to match the refractive index of optical hardware and/or intrinsic osmotic pressure of the tissue to eliminate image and/or tissue distortions. The refractive index adjustment agent and/or the osmotic pressure adjustment agent comprises at least one of iohexol, thiodiglycol, glycerol, poly(ethelyne glycol), triethanolamine, and quadrol (N,N,N',N-Trtrakis(2-Hydroxypropyl)ethylenediamine. The adjustable refractive index and/or the adjustable osmolality can be provided by a refractive index adjustment agent and/or an osmotic pressure adjustment agent. Each of the refractive index adjustment agent and the osmotic pressure adjustment agent can be added to the water at a concentration of 0 to 20 weight percent. In some instances, each of the refractive index adjustment agent and the osmotic pressure adjustment agent can be added to the water at a concentration of 0 to 10 weight percent. In other instances, each of the refractive index adjustment agent and the osmotic pressure adjustment agent can be added to the water at a concentration of 0 to 5 weight percent. In further instances, each of the refractive index adjustment agent and the osmotic pressure adjustment agent can be added to the water at a concentration of 10 to 20 weight percent. In still further instances, each of the refractive index adjustment agent and the osmotic pressure adjustment agent can be added to the water at a concentration of 15 to 20 weight percent.

The clearing agent may also include a detergent to help permeabilization of cells in the sample. Examples of the detergent can include triton X-100, digitonin, saponin, or the like. The detergent can have a concentration of between 0 and 2 weight percent. However, in some instances, the detergent can have a concentration between 0 and 0.5 weight percent. In other instances, the detergent can have a concentration between 0.5 and 2 weight percent. In still other instances, the detergent can have a concentration between 0.25 and 0.75 weight percent.

Referring again to FIG. 1, the imaging unit 14 can record raw data corresponding to one or more images of the sample after the sample emerges from the preparation/processing unit. The tissue sample can remain immersed in the clearing agent during imaging; however, in some instances, the tissue sample can be removed from the clearing agent before imaging. The imaging unit 14 can also be linked to an image processing unit to transfer the raw data for analysis. The image processing unit can process the raw data for analysis and/or display one or more images based on the raw data.

IV. Methods

Figure 3:
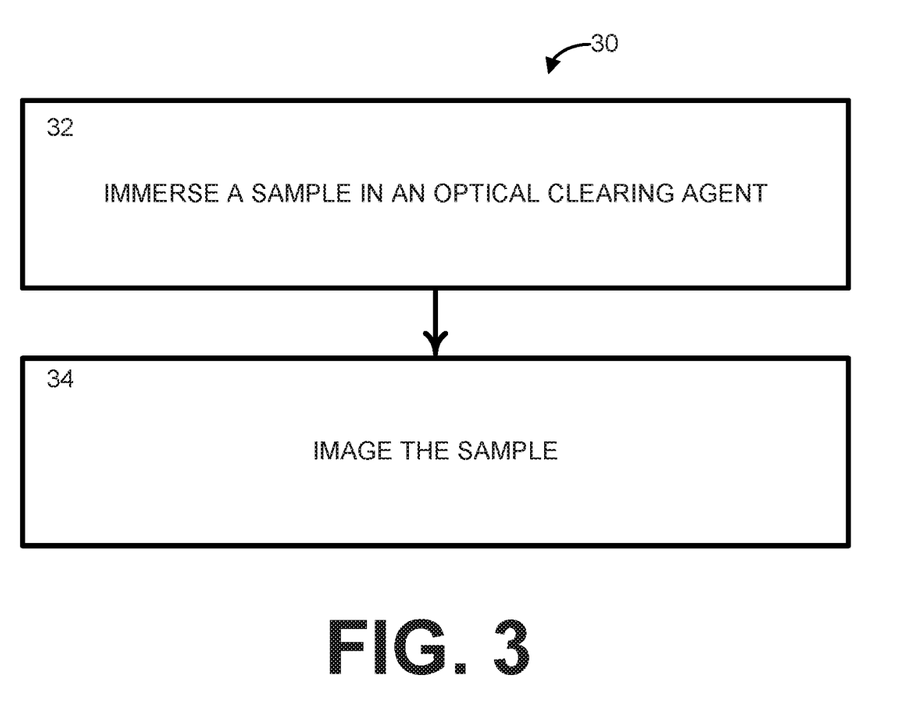
FIG. 3 is a process flow diagram illustrating an optical clearing method called LIMPID according to another aspect of the present disclosure.

Another aspect of the present disclosure can include an optical clearing method 30 called lipid-preserving index matching for prolonged imaging depth (LIMPID). The method 30 can be executed using at least a portion of the system 10 shown in FIGS. 1 and 2 and described above.

At step 32, a sample can be immersed in an optical clearing agent. LIMPID uses a clearing agent that combines the use of an iodine-containing, non-ionic radiocontrast agent and urea to strengthen its clearing capability with both the iodine-containing, non-ionic radiocontrast agent and the urea working together to provide a strong synergistic effect on speed and clearing capability. Additionally, the clearing agent has an adjustable refractive index and osmolality, which improves the image quality by matching the refractive index to optical hardware to eliminate tissue distortions. At step 34, the sample can be imaged. In some instances, the sample can be within the clearing solution as it is imaged.

VII. Experimental

The following experiment shows an optical clearing method called lipid-preserving index matching for prolonged imaging depth (LIMPID). LIMPID provides simplicity, speed, instrument compatibility, and imaging performance, including imaging depth and signal to noise ratio. The following experimental results are shown for the purpose of illustration only and are not intended to limit the scope of the appended claims.

Figure 4:
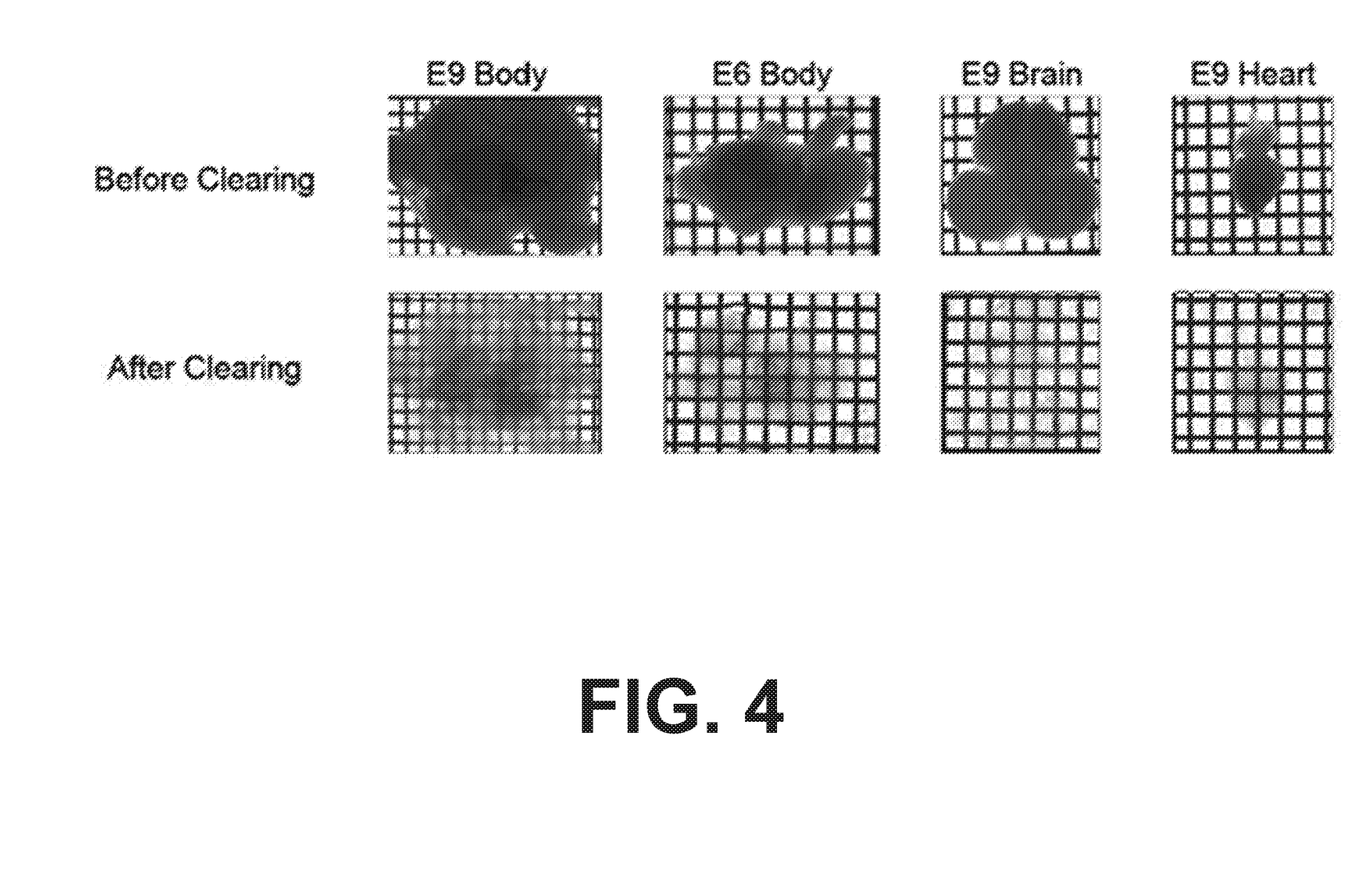
FIG. 4 shows examples of LIMPID clearing in different samples.

As shown in FIG. 4, samples, including an E9 quail body, an E6 quail body, an E9 quail brain and an E9 quail heart, were labeled, as shown in the "before clearing" row of images. The samples were placed in the LIMPID clearing agent (including at least water, an iodine-containing, non-ionic radiocontrast agent, and urea) and cleared overnight. The after clearing row of images show the effect of the clearing agent on the samples. LIMPID is a simple procedure, that works at a high speed and high transparency with a wide range refractive index, flexible imaging setup, minimum toxicity, mild to the lipid bilayer, with low size changes, low viscosity, and low cost.

Figure 5:
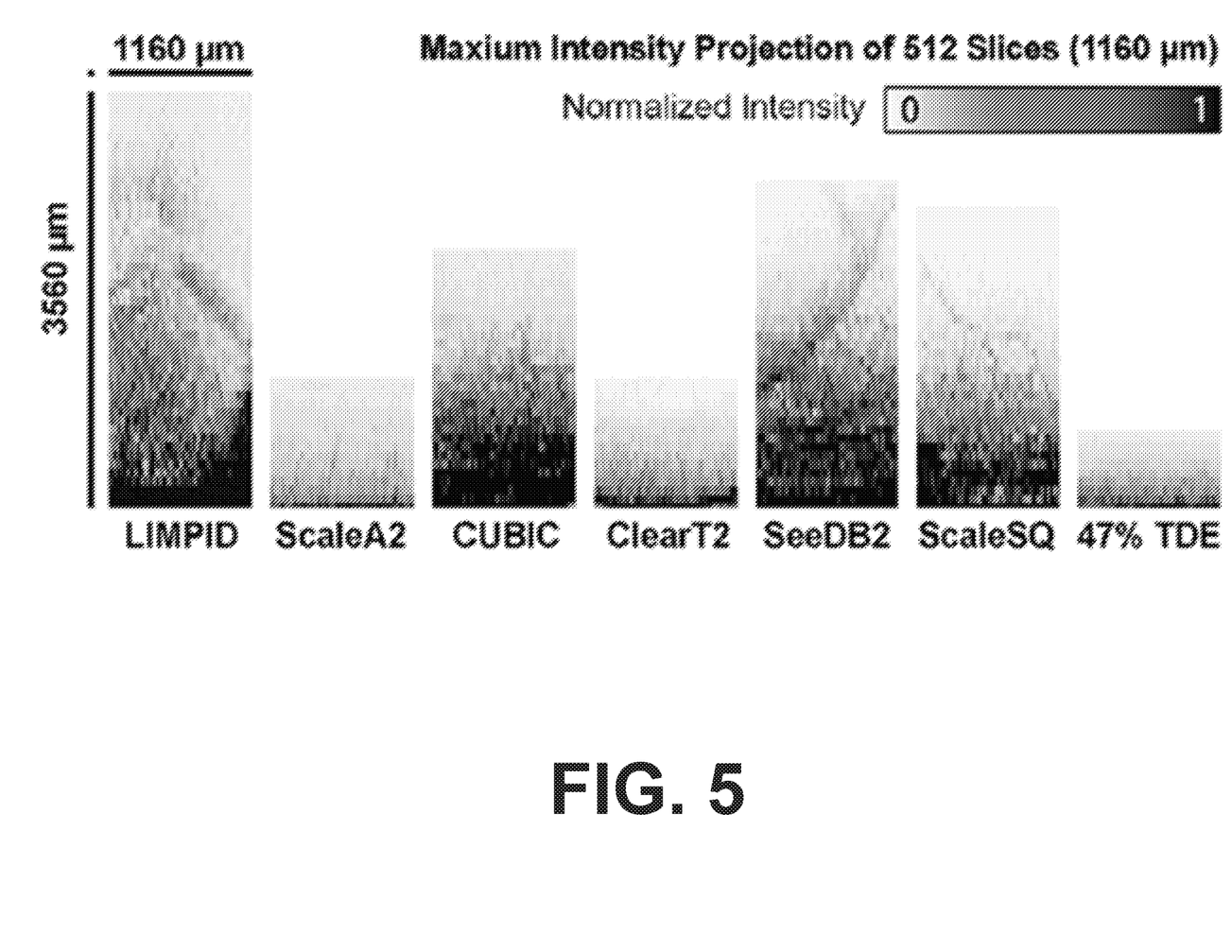
FIG. 5 shows a maximum intensity projection of 512 slices (1160 μm width×3560 μm depth) of same age quail brains treated with different clearing agents.
Figure 6:
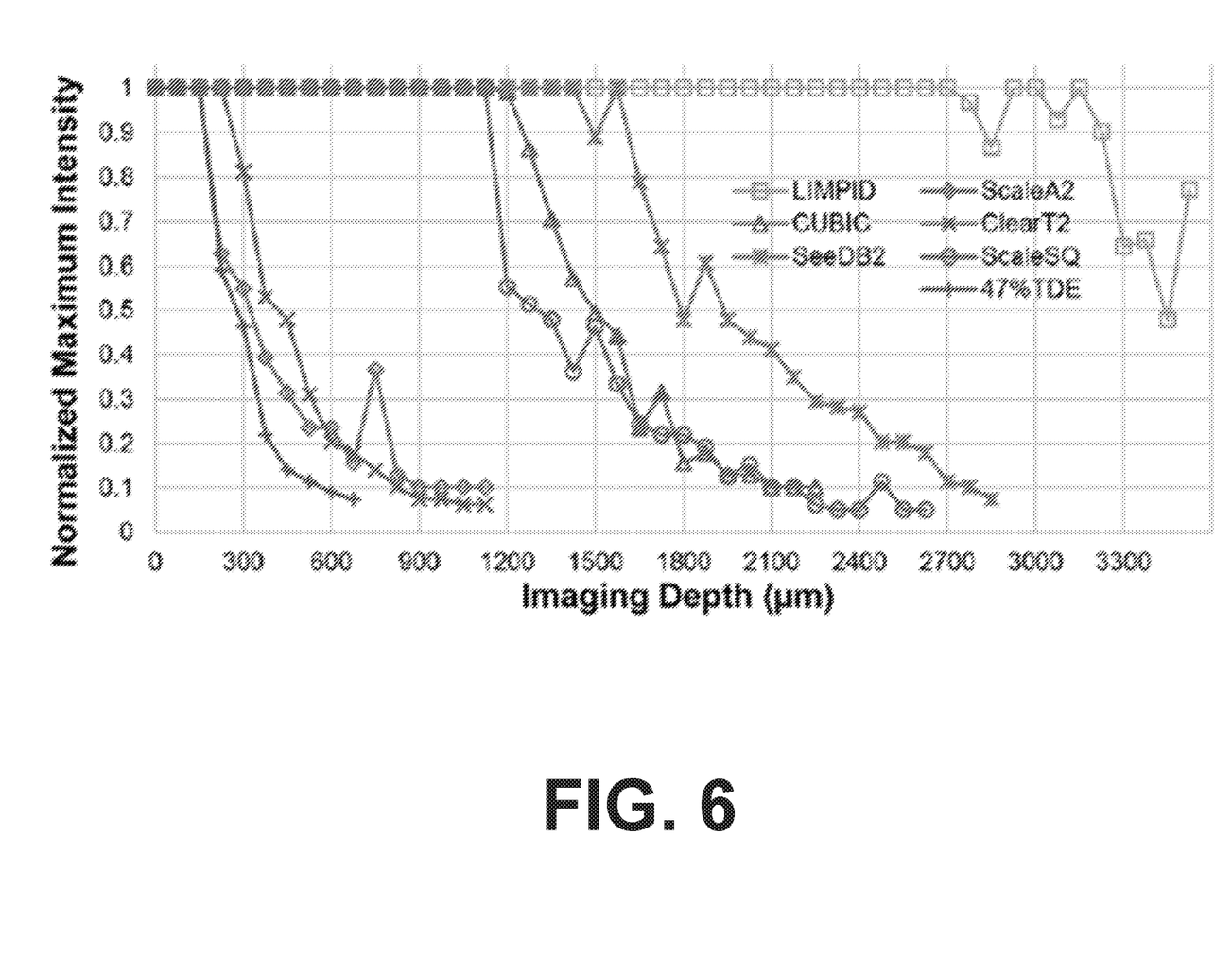
FIG. 6 shows a plot of the maximum pixel intensity at different imaging depths within the 512 slices (1160 μm width×3560 μm depth) of same age quail brains treated with different clearing agents.

FIGS. 5 and 6 show a comparison between different clearing methods—LIMPID, ScaleA2, CUBIC, ClearT2, SeeDB2, ScaleSQ, and 47% TDE. With all clearing agents, Tg(tie1: H2B-eYFP) quail brains at the same embryo stage (E9) were processed with clearing protocols according to the corresponding original published journal articles. The cleared samples were imaged with the same inverted fluorescent confocal microscope. For all confocal imaging tasks, the same optical setup (10× air objective), the same laser power (~20 mW), the same detector gain (100%) and the same software configuration (e.g., line average, accumulation, etc.) were used. Volumetric image datasets were taken for each cleared sample. Starting by focusing at the outermost surface of the sample, a 512×512 pixel (1160×1160 mm) 2D confocal scan was taken at the microscope objective focal plane. Then, the focal plane was moved 75 mm deeper into the sample repeatedly and a 512×512 pixel (1160×1160 mm) 2D confocal scan was taken after each movement until the maximum pixel value on the confocal scan dropped below the noise flour. In FIG. 5, for each type of cleared sample, a volumetric image dataset was rendered in maximum intensity projection (at the XZ plane) for visual comparison. Each pixel on each panel represents the maximum pixel value (normalized from 0 to 1) at the corresponding pixel location from the 512 XZ images from each volumetric dataset. FIG. 6 shows a plot of the maximum pixel value of 262,144 pixels at different imaging depths for each type of cleared sample. As shown in both FIGS. 5 and 6, LIMPID provides the best imaging depth.

Figure 7:
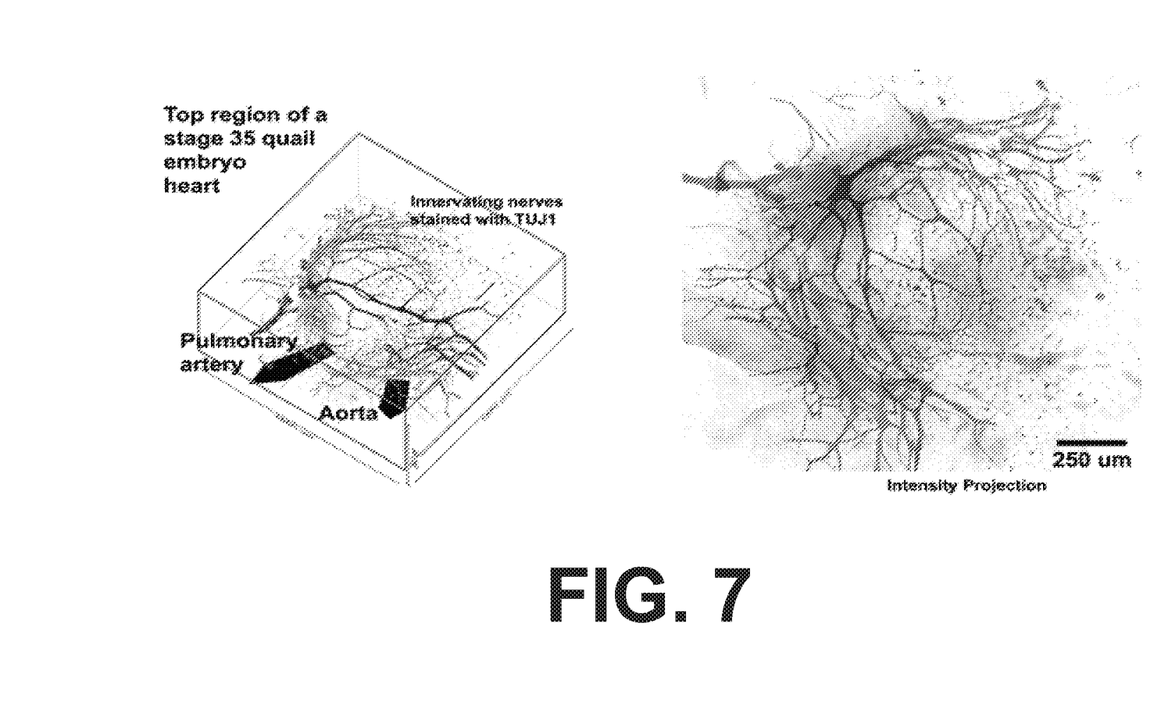
FIG. 7 shows that a stage 35 quail embryo heart previously stained with a fluorescent conjugated antibody can be imaged using fluorescent confocal microscopy after LIMPID clearing.
Figure 8:
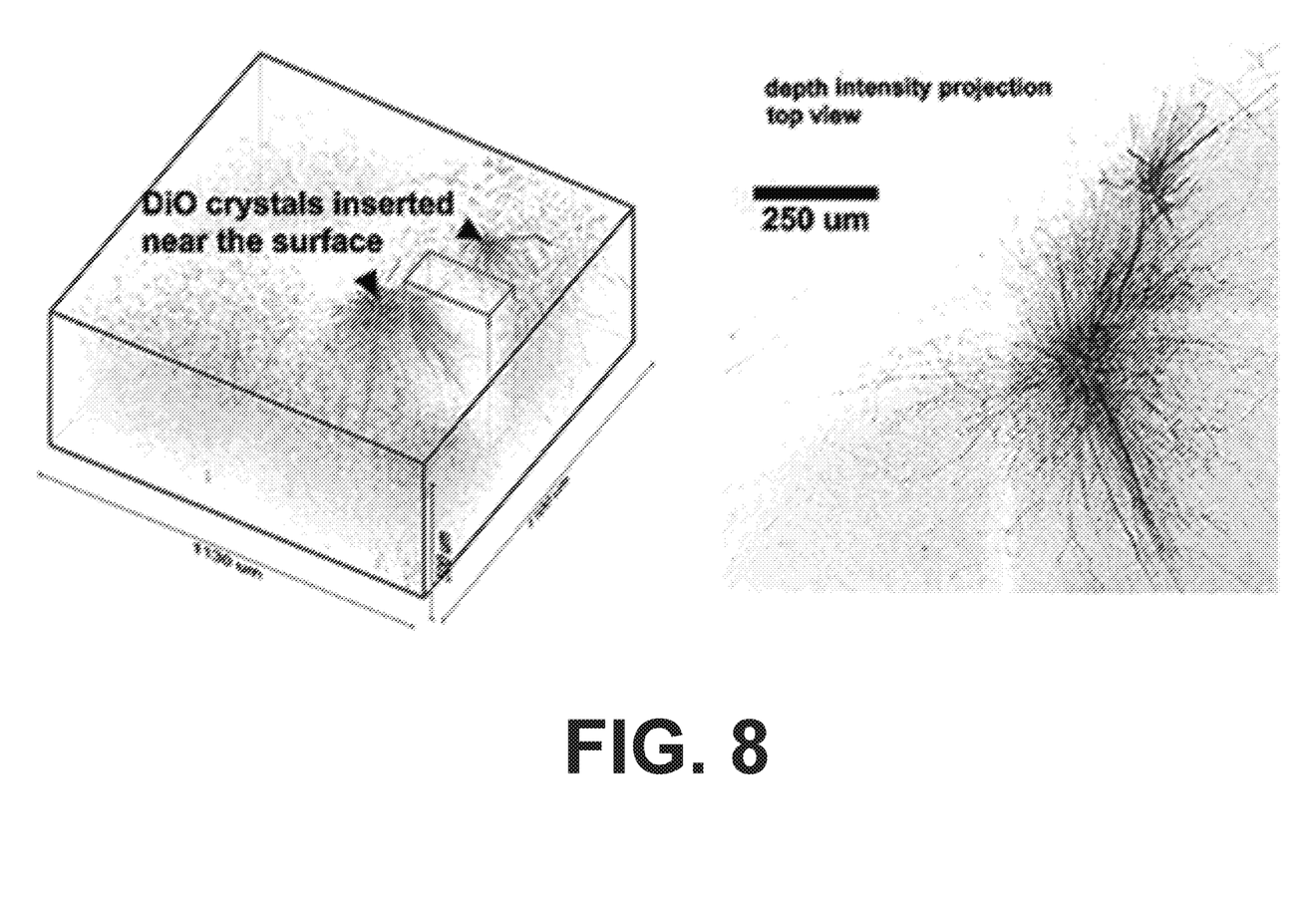
FIG. 8 shows that an adult male brain slice stained with lipophilic fluorescent dye can be imaged using fluorescent confocal microscopy after LIMPID clearing.

Experiments showing the images obtained with LIMPID cleared samples are shown in FIGS. 7 and 8. As shown in FIG. 7, a sample (stage 35 quail embryo heart) previously being stained with fluorescent conjugated antibody can be imaged using fluorescent confocal microscopy after LIMPID clearing. LIMPID preserved the fluorescent probe and antibody binding through the optical clearing process. As shown in FIG. 8, a sample (adult mouse brain slice) stained with a lipophilic fluorescent dye (DiO) can be imaged using fluorescent confocal microscopy after LIMPID clearing. A lipophilic fluorescent dye can bond and diffuse through phospholipid bilayers in biological structures. LIMPID can preserve the phospholipid bilayer during the optical clearing process and enables successful labeling and imaging of the related structures.

From the above description, those skilled in the art will perceive improvements, changes and modifications. Such improvements, changes and modifications are within the skill of one in the art and are intended to be covered by the appended claims.

The following is claimed:

1. An optical clearing solution for a labeled sample, the optical clearing solution comprising:
   water;
   an iodine-containing, non-ionic radiocontrast agent comprising 40 to 80 weight percent iodixanol in solution with 1 to 20 weight percent triethanolamine;
   1 to 20 weight percent of iohexol; and
   urea for lipid preservation, wherein the urea has a concentration of 10 to 50 weight percent,
   wherein the optical clearing solution is configured to preserve lipids within the labeled sample without reducing diffusion speed through a synergistic combination of at least the iodine-containing, non-ionic radiocontrast agent comprising the 40 to 80 weight percent iodixanol in solution with the 1 to 20 weight percent triethanolamine and the urea having the concentration of 10 to 50 weight percent.

2. The optical clearing solution of claim 1, wherein the 1 to 20 weight percent of the iohexol adjusts a refractive index of the optical clearing solution.

3. The optical clearing solution of claim 1, wherein a refractive index of the optical clearing solution matches a refractive index of optical hardware to eliminate tissue distortion.

4. The optical clearing solution of claim 1, further comprising 0 to 1 weight percent of a detergent to help permeabilization of cells in a tissue.

5. The optical clearing solution of claim 4, wherein the detergent is triton X-100, digitonin or saponin.

6. A method comprising:
   immersing a labeled sample in an optical clearing solution before imaging,
   wherein the optical clearing solution comprises:
      water;
      an iodine-containing, non-ionic radiocontrast agent comprising 40 to 80 weight percent iodixanol in solution with 1 to 20 weight percent triethanolamine;
      1 to 20 weight percent of iohexol; and
      urea to preserve lipids of a labeled sample, wherein the urea has a concentration of 10 to 50 weight percent; and
   imaging the labeled sample with lipids within the labeled sample preserved without reducing diffusion speed.

7. The method of claim 6, wherein the imaging is fluorescent microscopy, confocal microscopy, light-sheet microscopy, two-photon microscopy, structured illumination microscopy, light-field microscopy, or optical coherence tomography.

8. The method of claim 6, wherein the 1 to 20 weight percent of the iohexol adjusts a refractive index of the optical clearing solution.

9. The method of claim 6, wherein the optical clearing solution matches a refractive index of optical hardware of an imaging modality to eliminate optical distortion.

10. The method of claim 6, wherein optical clearing solution further comprises 0 to 1 weight percent of a detergent to help permeabilization of cells in a tissue.

11. The optical clearing solution of claim 1, further comprising 0 to 20 weight percent of glycerol to adjust an osmolality of the optical clearing solution.

12. The method of claim 6, wherein the optical clearing solution further comprises 0 to 20 weight percent glycerol to adjust an osmolality of the optical clearing solution.

13. An optical clearing solution for a labeled sample, the optical clearing solution consisting of:
   water;
   an iodine-containing, non-ionic radiocontrast agent comprising 40 to 80 weight percent iodixanol in solution with 1 to 20 weight percent triethanolamine;
   1 to 20 weight percent of iohexol; and
   urea for lipid preservation, wherein the urea has a concentration of 10 to 50 weight percent,
   wherein the optical clearing solution is configured to preserve lipids within the labeled sample without reducing diffusion speed through a synergistic combination of at least the iodine-containing, non-ionic radiocontrast agent comprising the 40 to 80 weight percent iodixanol in solution with the 1 to 20 weight percent triethanolamine and the urea having the concentration of 10 to 50 weight percent.

* * * * *